USO05474519A

United States Patent [19]
Bloomer

[11] Patent Number: 5,474,519
[45] Date of Patent: Dec. 12, 1995

[54] METHOD FOR OBTAINING STEREOSCOPIC IMAGERY FROM A PAIR OF ENDOSCOPES

[76] Inventor: William E. Bloomer, 585 Bellefontaine St., Pasadena, Calif. 91105

[21] Appl. No.: 239,872

[22] Filed: May 10, 1994

[51] Int. Cl.$^6$ ....................................................... A61B 1/00
[52] U.S. Cl. ............................................. 600/111; 600/102
[58] Field of Search .................................. 128/3–11, 762, 128/772, 18, 20; 348/45; 604/43, 165, 283, 284

[56] References Cited

U.S. PATENT DOCUMENTS

| 1,139,015 | 5/1915 | Cerbo ........................................ 128/18 |
| 2,082,782 | 6/1937 | Allen ........................................ 128/20 |
| 3,520,587 | 7/1970 | Tasaki et al. . |
| 3,626,471 | 12/1971 | Florin ........................................ 128/4 |
| 4,061,135 | 12/1977 | Widran . |
| 4,263,899 | 4/1981 | Burgin .................................. 128/20 X |
| 4,386,602 | 6/1983 | Sheldon et al. ............................ 128/4 |
| 4,502,485 | 3/1985 | Burgin .................................. 128/20 X |
| 4,528,587 | 7/1985 | Jones, Jr. . |
| 4,539,976 | 9/1985 | Sharpe ....................................... 128/6 |
| 4,651,201 | 3/1987 | Schoolman . |
| 4,674,496 | 6/1987 | Svadjian et al. ....................... 128/4 X |
| 4,784,117 | 11/1988 | Miyazaki ................................ 128/4 |
| 4,862,873 | 9/1989 | Yajima et al. . |
| 4,924,853 | 5/1990 | Jones, Jr. et al. . |
| 4,926,257 | 5/1990 | Miyazaki . |

*Primary Examiner*—Richard J. Apley
*Assistant Examiner*—John P. Leubecker
*Attorney, Agent, or Firm*—Fulwider Patton Lee & Utecht

[57] ABSTRACT

A method is presented for stereoscopically observing a tissue in a patient's body cavity which includes the selection of a hand held holder formed with a pair of elongated open ended tubular housings for receipt of conventional elongated monoscopic endoscopes. The housings are rigidly connected together and converge distally inwardly toward one another at a predetermined angle for receipt of the respective endoscopes so they can project from the distal end thereof for observation of the patient's tissue. The surgeon may position the endoscopes in the respective housings and affix them in position to be held angled toward one another. An incision may be made for access to the patient's chest or abdomen and the tissue to be examined manipulated away from the opening. A multiplexer device is selected and coupled with the endoscopes and a monitor selected for use with a muliplexing device to display images thereon. Three dimensional viewing glasses may be selected for use with the monitor to view the tissue site.

2 Claims, 4 Drawing Sheets

METHOD FOR OBTAINING STEREOSCOPIC IMAGERY FROM A PAIR OF ENDOSCOPES

BACKGROUND OF THE INVENTION

1. Field of the Invention

The present invention relates to a method and apparatus for stereoscopic viewing of a patient's body cavity and particularly such a method incorporating conventional endoscopes.

2. Description of the Prior Art

Endoscopes have commonly been utilized in surgery to enable the surgeon to view the body cavity through relatively small incisions thereby minimizing trauma and post operative pain and recovery.

Conventional endoscopes typically provide for viewing the internal organs in the form of a planar object without a three dimensional view thus limiting the effectiveness, efficiency and convenience for the surgeon in achieving the objective of the operation. The advantages attendant stereoscopic viewing of a patient's internal organs through a small incision have long been known. The recognition of these advantages have led to the development of various sophisticated methods and equipment in effort to devise an endoscopic probe for insertion through a small incision into a body cavity to enable the surgeon to view the surgery by three dimensional television. However, the devices proposed for such endoscopic systems are typically technically sophisticated requiring significant development costs and capital investment beyond the financial capability of many of the present day medical institutions. Thus, surgeons on the staff of the majority of such institutions are currently left without the capability of performing endoscopic surgery with the benefit of stereoscopic observation of the surgery site.

Substantial work has been performed in the field. It has been proposed to provide a binocular endoscope housed in a tube combined with a conduit for irrigation and including a gear mechanism for rotating an optical shaft within the tube. A device of this type is shown in U.S. Pat. No. 4,061,135 to Widran. The system disclosed is rather sophisticated, expensive and fails to incorporate video cameras and monitors enabling effective use of existing non-stereoscopic endoscopes in any combination which will achieve a perspective view of the surgical site.

It has been proposed to provide a custom made stereoscopic endoscope housed in a sheath bundling a pair of image guides, a light guide and various other channels for air, water, gas or other liquids. A device of this type is shown in U.S. Pat. No. 4,651,201 to Schoolman. While recognizing the advantages of stereoscopic endoscopes, the devices described is relatively complicated, cumbersome, expensive to manufacture and inconvenient to use.

It has also been proposed to provide a arthroscope for viewing of human or animal joints which includes a prism arrangement in effort to achieve stereoscopic capability. A device of this type is shown in U.S. Pat. No. 4,924,853 to Jones. A device of this type requires relatively sophisticated technology and is expensive to manufacture.

Other efforts to provide a stereoscope endoscope device includes the proposal of a pair of flexible endoscopes incorporated in a pair of fiber optical systems to be viewed through oculars. A device of this type is shown in U.S. Pat. No. 3,520,587 to Tasaki. While providing certain benefits, such a device suffers the shortcoming that it is expensive to manufacture and compromises the advantages of rigidity in endoscopes for manipulation in a body cavity.

Other efforts to achieve stereoscopic viewing of internal organs includes the provision of a sophisticated flashing strobe lamp with a synchronized rotating prism as shown in U.S. Pat. No. 4,862,873 to Yajima and an electronic endoscopic device as shown in U.S. Pat. No. 4,926,257 to Miyazaki.

The general thinking of current day manufacturers of stereoscopic thoracoscopes aims at miniaturization for introduction of a probe through a single small incision. Manufacturers such as Zeiss and Baxter have proposed such thoracoscopic systems and they estimate that, when FDA approval is achieved, each such system may well require a capital investment of $40,000.00 to $50,000.00. Thus, there exists a need for a practical and inexpensive stereoscopic endoscopic apparatus which will make the benefits of stereoscopic viewing available to a wider range of medical institutions and to surgeons practicing in less affluent geographic areas.

Such a method and apparatus should provide adequate three dimensional visualization for video assisted surgery. An additional benefit would be the capability of adding stereoscopic endoscopy to a single thoracoscope during surgery in the event difficulty is encountered in making the dissection or other surgical procedure.

SUMMARY OF THE INVENTION

The method of the present invention is characterized by a procedure for utilizing monoscopic endoscopes for stereoscopic observation of a body cavity. The method involves selecting a hand held holder of the type including a pair of elongated open-ended tubular housings rigidly secured together and configured for telescopical receipt of tubular conventional monoscopic endoscopes from one end thereof to converge toward the opposite ends to provide an unobstructed view from such opposite end for close viewing of the work area within the body cavity. The endoscopes are slid into the respective housings from the divergent ends, adjusted for proper image orientation and affixed in place. An incision may then be made in the body cavity and the endoscopes held by such holder are then manipulated for insertion of the distal ends of the endoscopes through the body cavity for viewing of the image generated through three dimensional glasses to provide stereoscopic viewing of the operation site. The holder may be in the form of open ended convergent tubes having some screws threadably engaged through threaded bores in the walls thereof for selective tightening against the exterior walls of the endoscope to affix such endoscopes in their fixed relationship within the holder.

Other objects and features of the invention will become apparent from consideration of the following description taken in conjunction with the accompanying drawing.

DESCRIPTION OF THE PREFERRED EMBODIMENT

Figure 1:
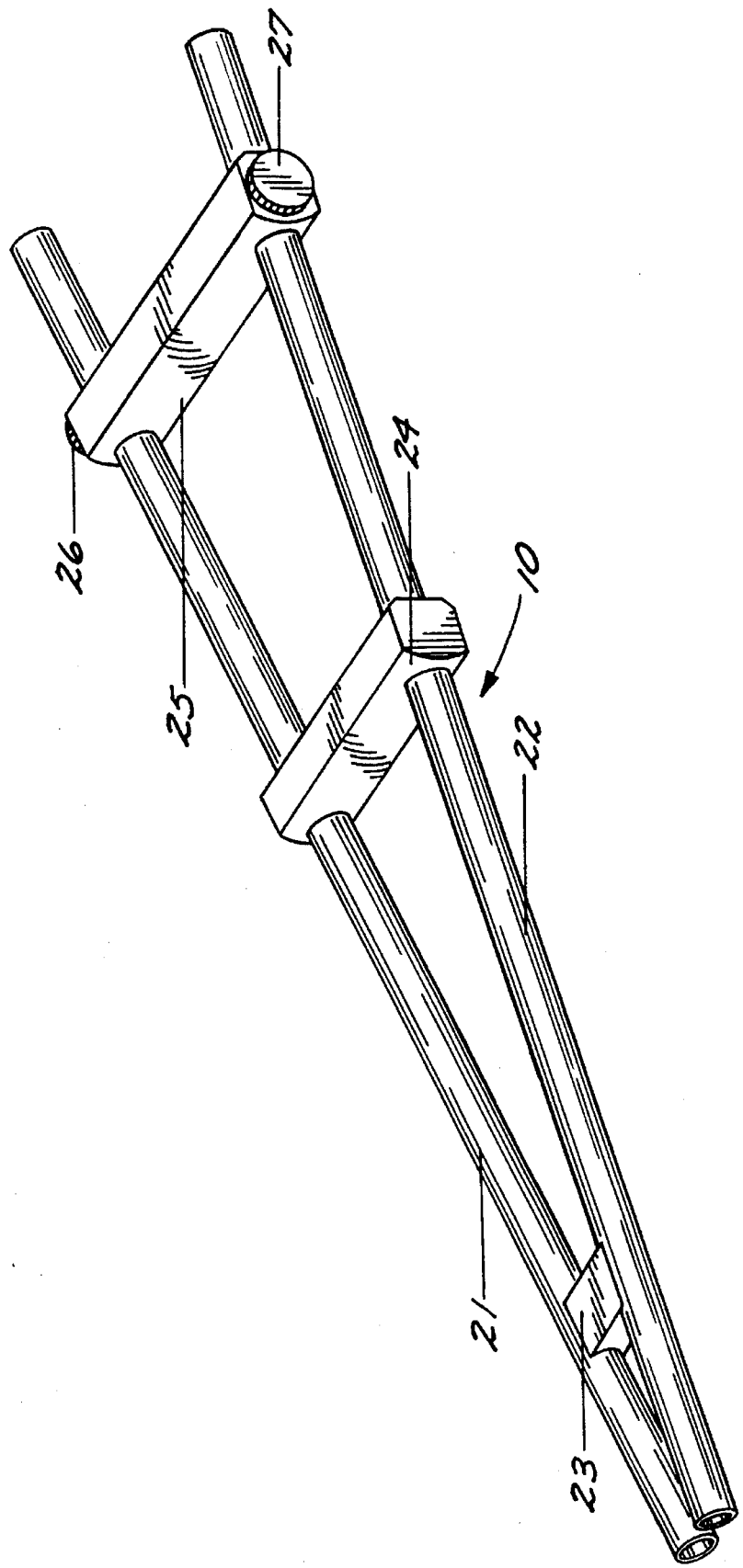
FIG. 1 is a perspective view of a stereoscopic endoscope holder embodying the present invention.
Figure 2:
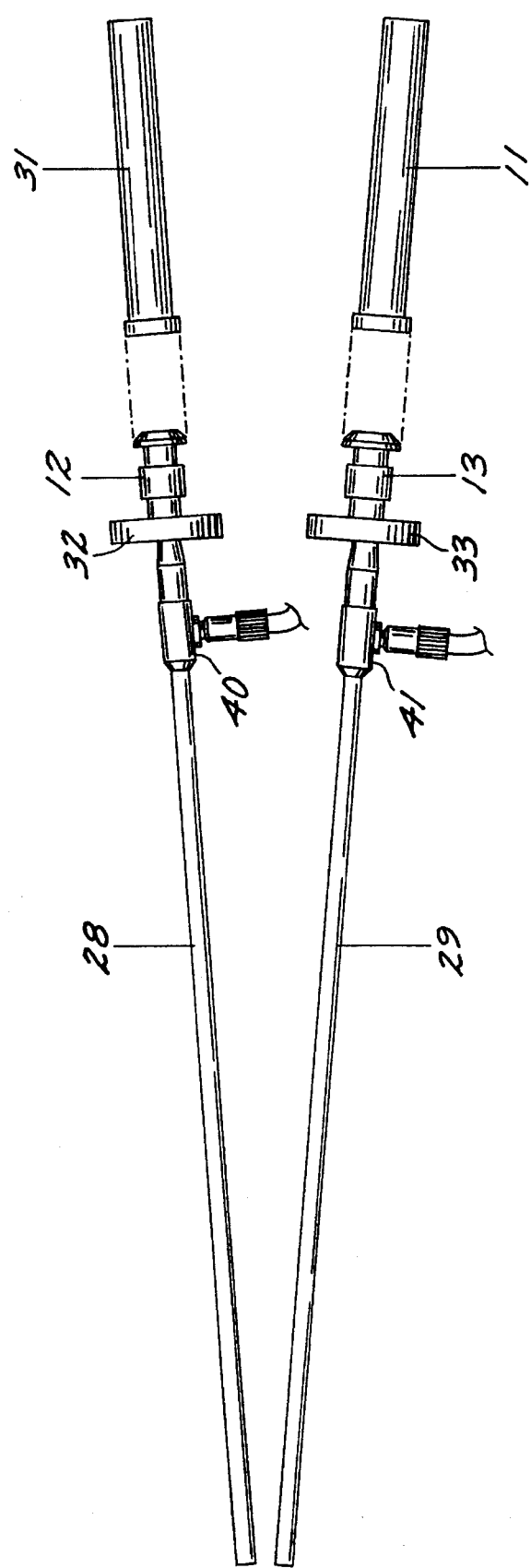
FIG. 2 is a top plan view of endoscopes and cameras which may be utilized with the holder shown in FIG. 1.
Figure 3:
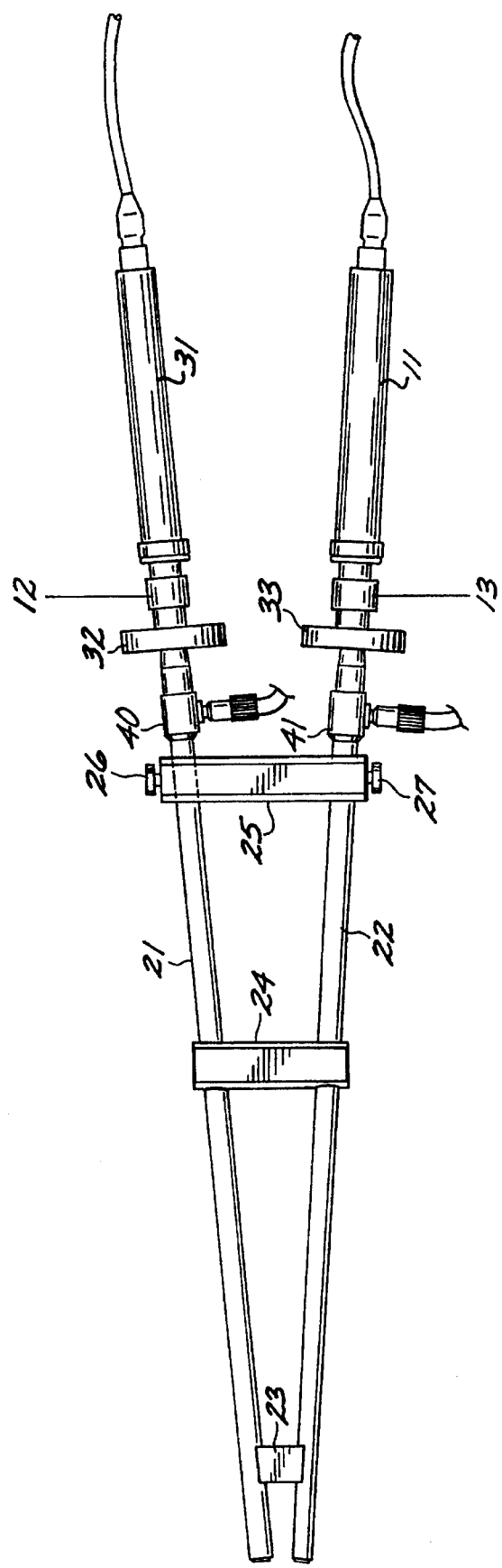
FIG. 3 is a top plan view, in reduced scale, of the endoscope holder shown in FIG. 1 with the endoscope inserted.
Figure 4:
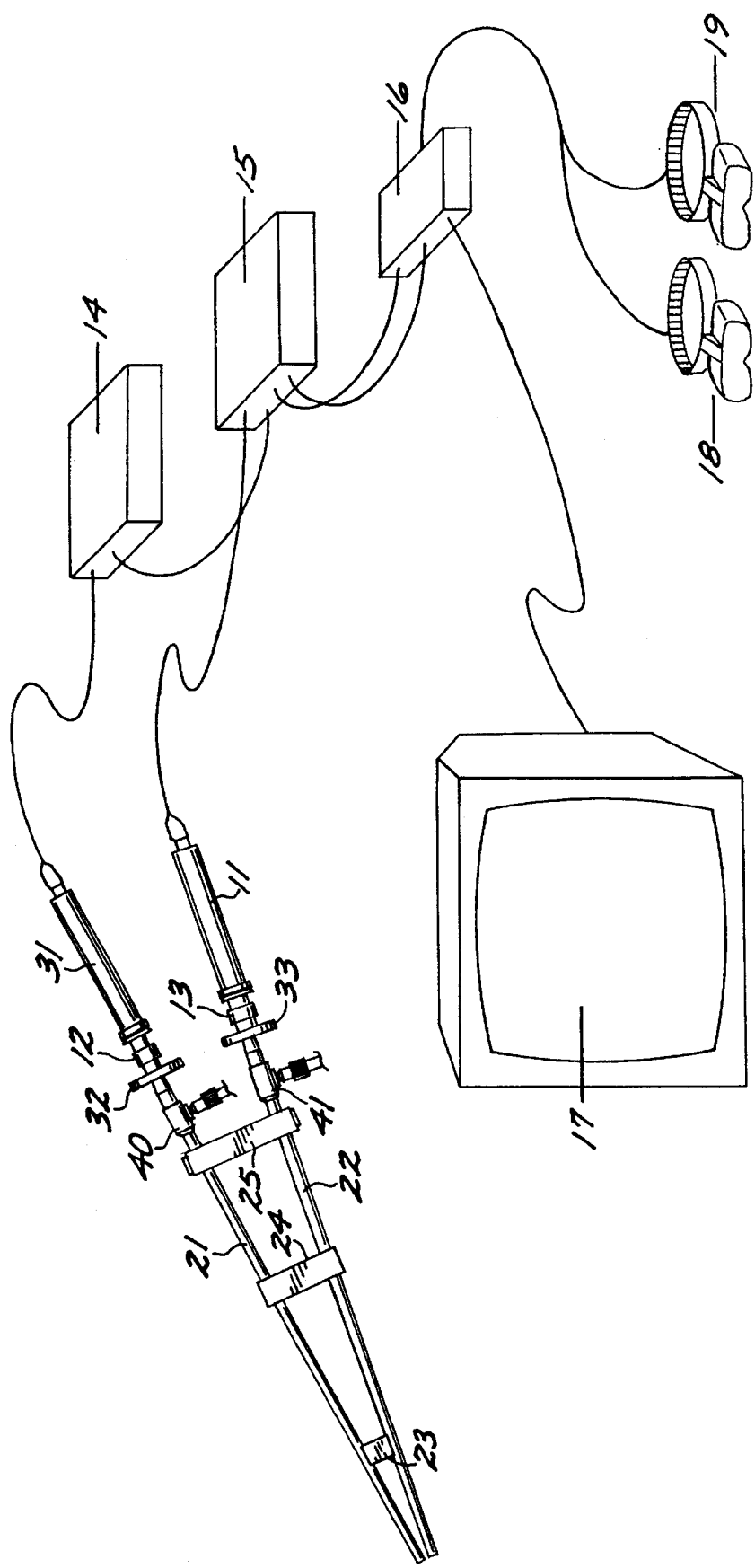
FIG. 4 is a diagrammatic view showing a system incorporating the stereoscopic endoscope holder shown in FIG. 1 but depicted in reduced scale.

Referring to FIGS. 1, 2 and 4, the method of the present invention involves an endoscope holder, generally designated 10, including distally converging open ended stainless steel tubes 21 and 22 carried on a frame and locked in position by means of respective thumb screws 26 and 27. The method involves fixedly securing respective endoscopes 28 and 29 in fixed telescopical relation within the respective tubes 21 and 22 for fixing the respective optical axes thereof in fixed converging angular relationship. The endoscopes with small television cameras 31 and 11 attached may then be coupled through a multiplexer 16 (FIG. 4) to a television monitor 17 for viewing through respective pairs of three dimensional goggles 18 and 19. Consequently, the method may employ conventional endoscopes 28 and 29 to be held in the holder 10 for insertion through a small incision in a body cavity for three dimensional viewing the surgery site.

With the current high cost of medical care and public consciousness of medical expenses, concern is prevalent over the capital investment by medical institutions. Consequently, many institutions cannot afford or are not in a position to invest the capital required to have access to the latest and most expensive medical equipment to support surgeons in their daily tasks.

It is known that for certain interventional procedures, three dimensional observation of the surgery site is beneficial. While three dimensional endoscopic devices are currently under development and may be available to support endoscopic surgery, such devices are prohibitively expensive for many medical institutions. However, there exists at numerous different institutions the various medical equipment available to perform endoscopic surgery. These institutions already possess the required endoscopes, cameras and television monitors, and the only additional equipment required for three-dimension viewing is that of a multiplexer and appropriate binoculars. This would then enable the performance of endoscopic surgery with the benefit of three dimensional observation provided the endoscopes could be securely positioned in fixed relative relationship to pick up the image at the surgery site and convey it to the three dimensional monitor for viewing by three dimensional binoculars. It is thus an object of the present invention to provide a method and apparatus whereby a surgeon might make use of existing endoscopic and viewing equipment already in inventory to enable the performance of endoscopic surgery with the benefit of three dimensional viewing.

To this end, I have provided a framework constructed of three nylon (LP-410) cross bars 23, 24 and 25 of progressively greater length and carrying at their opposite extremities the distally converging open ended endoscopic support tubes 21 and 22. Conventional endoscopes are of tubular construction including a probe with an outside diameter of 10 mm and a length of 31 cm distal to its fiber optic light inlet attachment. Consequently, the endoscopic support tubes 21 and 22 are constructed with an internal diameter of approximately 11 mm so as to accommodate insertion of a 10 mm scope and a length of about 30.5 cm so as to allow the scope to protrude slightly from the distal end of the holder. It has been determined that the angle at which the optical axes of endoscopes should be positioned in relation to one another to achieve stereoscopic imaging is about 8°. Consequently, the tubes 21 and 22 are carried in the frame bars 23–25 to converge distally together at a relative angle of 8°. As will be apparent to those skilled in the art, it may be desirable to incorporte the endoscopes directly onto the television cameras thus eliminating the more bulky couplers, it may be desirable in construction to reduce somewhat this angle of convergence for the two scope-holding tubes, so as to allow more freedom of manipulation through a small incision.

Referring to FIG. 1, the proximal frame bar 25 is formed at its opposite ends with threaded bores which extend through the exterior walls of the respective tubes 21 and 22 and are configured for receipt of the threaded stems of respective stainless steel thumb screws 26 and 27 which are configured for tightening thereof to press the ends of such threaded stems against endoscopes to be held captive in the respective tubes 21 and 22.

The respective tubes 21 and 22 are configured for telescopical receipt through the internal bore thereof of the stems of conventional 0—degree endoscopes 28 and 29 of the type typically available from Storz or Mueller. These endoscopes are formed near their respective proximal ends with respective flanges 32 and 33 to which may be attached conventional television attachment couplers 12 and 13, respectively, for coupling with respective television cameras 31 and 11. A television camera useful for this purpose is the Sony CCD Color Camera, Model No. 92AXC-99. For coupling such cameras, it has been found that couplers available from Dynamics Coupler, Catalog No. 3344 are useful in that they provide a firm grip on the endoscopes to prevent relative movement and consequent image distortion.

Referring to FIG. 4, in practice, the television cameras 31 and 11 are connected with respective power sources 14 and 15. The power sources are then coupled with a conventional multiplexer 16. Useful for this purpose is a multiplexer marketed by T.V. Corp., P.O. Box Q, San Rafael, Calif. 94913 under Model No. 100 as a 12 volt DC stereoscopic multiplexer. The multiplexer is then coupled with a conventional television monitor to provide for three dimensional depth of viewing when observed with the appropriate binoculars. The television monitor 17 is the same type that is used for conventional 2-D endoscopy. As will be apparent to those skilled in the art, the television monitor 17 may be of the type typically employed for conventional 2-D endoscopy. The goggles 18 and 19 may be three dimensional scope goggles available from Toshiba, Model No. VDG3D1 or those available from Nintendo Famicon and its three dimensional system under Model No. HVG-031. These goggles are attached by respective electrical leads to the multiplexer. More expensive wireless equipment is available through 3-D TV Corporation, P.O. Box Q, San Rafael, Calif. 94913-4316, if so desired.

In operation, it will be appreciated that the endoscope holder of the present invention may be conveniently utilized in performing procedures requiring access to the body cavity in the chest area (thoracoscopy) or in the abdominal area. The holder may be of construction so it can be sterilized by steam autoclaving, Steraad sterilization using hydrogen peroxide or sterilization by ethylene oxide. It will be appreciated that the couplers 12 and 13 and cameras 31 and 11 should not be subjected to sterilization to thereby avoid unnecessary deterioration and prolong their useful life. The surgeon may employ the usual technique covering the unsterile cameras and couplers with a sterile sleeve or plastic overlay. The sterile plastic sleeve is attached with sterile tape to the ocular end of each scope and the cameras and couplers with the electrical leads attached is passed carefully down the sterile sleeve without contamination of the exterior thereof. The cameras, screwed securely to the couplers, are clamped to the endoscopes using the clamping mechanism incorporated in the conventional couplers for attachment to the ocular rings of such scopes.

For the configuration disclosed in the preferred embodiment, the endoscopes 28 and 29 may be of the type characterized by a 10 mm, 0° angle endoscope and will be held in the tubes 21 and 22 oriented with their axial optical axes at an distally converging angle of 8° to one another. This angle has been found to provide good stereoscopic vision and depth of field. For the configuration shown, the couplers 12 and 13 are spaced apart a distance sufficient to provide a space therebetween for access by the surgeon's fingers to make the necessary rotational adjustment of the respective cameras 31 and 11 and endoscopes 28 and 29. Such endoscopes 28 and 29 typically incorporate respective fiber optic light couplings 40 and 41, respectively. It will be appreciated that the endoscopes 28 and 29 may be telescoped to the desired depth in the respective tubes 21 and 22 and that such depth may be limited by engagement of, for instance, the metal arm receptacle for the fiber optic light cord with the proximal ends of the respective tubes. The endoscopes 28 and 29 may be rotated within the tubes 21 and 22 until the desired corresponding vertical orientation of the images are achieved. The thumb screws 26 and 27 may then be tightened to firmly engage the free ends of the respective stems with the respective shanks of the endoscopes 28 and 29 to secure them positively in position within the rigid connected tubes 21 and 22 to thus fixedly hold such endoscopes in fixed angular relation to one another.

For thoracoscopy surgery, it will be appreciated that the anesthesiologist will typically insert a double lumen endothrachial tube with one channel clamped off for the purpose of collapsing the lung on the side where the incision is to be made. Similarly, in abdominal use, a diaphragm between the edges of the incision and the scope holder may be required to maintain a volume of air within the abdominal cavity to allow space for manipulation of the holder and visualization of the surgery site. In this regard, it is noted that it is desirable to maintain air pressure within the abdominal cavity to maintain the viscera at a distance from the scope so as to not block visualization of the surgery site. Air leaks around the scopes can be limited or even totally prevented by using a cannula holding device as sold by Conmeal Corporation of Utica, N.Y. or possibly a cannula skirt available from Wayne Maxson, 5465 Leitner Drive, West Coral Gables, Fla. 33067.

In any event, for the thoracoscopy surgery the surgeon may make a short incision of about 2 ½ or 3 cm long at the appropriate level between the appropriate ribs. The incision then provides access for insertion of the endoscopes 28 and 29 held in the holder 10 without any necessity of spreading the ribs apart. As a consequence, postoperative pain experienced by the patient will be minimized. It will be appreciated that, at this stage, the power sources 14 and 15 have been connected to the respective cameras 31 and 11 and input to the multiplexer 16 and the multiplexer outlets connected with the respective three dimensional television monitors 17 and three dimensional goggles 18 and 19. The holder 10 may then be extended to the surgery site with the endoscopes 28 and 29 held firmly in relative fixed relationship for stereoscopic viewing of the site. The surgeon and his or her assistant viewing through the goggles 18 and 19 will then have the benefit of three dimensional viewing to thus expedite the surgery time, promote safety and enable the performance of operations which might otherwise be unattainable. These advantages coupled with the decreased operating room time required and the reduction in necessity of capital investment are all advantages attendant applicant's new holder and method.

Typically, the site will be illuminated by fiber optic illumination incorporated in the endoscopes and transmitted through the couplings 40 and 41. The respective images will be picked up by the optics of the respective endoscopes to be viewed by the respective cameras 31 and 11 to be transmitted through the respective power sources 14 and 15 to the multiplexer 16 for multiplexing and transmission of the multiplexed signals to the television monitor and goggles 18 and 19.

It will be appreciated by those skilled in the art that, if desired, the surgeon may initiate the procedure with a single endoscope in the conventional fashion, and assuming the procedure goes well he or she may complete the entire operation with a single endoscope. However, if difficulty should be encountered it is possible to enlarge the incision slightly to accommodate the holder of the present invention and place in it the original endoscope and then add a second endoscope of identical type to the holder to thereby enable the surgeon to proceed with the benefit of video assisted stereoscopic surgery.

Various modifications and changes may be made with regard to the foregoing detailed description without departing from the spirit of the invention.

What is claimed:

1. A method of stereoscopically observing a tissue in a patient's body cavity involving utilization of a pair of conventional elongated monoscopic endoscopes including elongated optical tubes of a predetermined size and configuration and having respective axial optical axes, including the following steps:

selecting a hand held holder including a pair of elongated open ended tubular housings carried by a rigid frame and sized and configured for telescopical receipt of the respective said optical tubes of said endoscopes from one end thereof to view out the respective opposite ends thereof, said housings converging towards one another at a predetermined angle from said one ends toward the said respective opposite ends and unobstructed at said opposite ends for close viewing of tissues within said cavity;

sliding said endoscopes into the respective said housings from the respective said one ends;

affixing the respective said endoscopes in fixed relation in the respective said housings;

making an incision for access to said body cavity for insertion of said holder and endoscopes;

independent of said holder, moving said tissue away from said incision;

selecting a multiplexing device;

coupling said multiplexing device to the respective said endoscopes;

selecting a monitor; and coupling said monitor to said multiplexing device for displaying of images from said multiplexing device;

selecting three dimensional viewing glasses for viewing the images on said monitor; and grasping said holder and inserting the distal extremities of said endoscopes in said holder through said incision to view said tissue through said three dimensional glasses whereby said conventional elongated monoscopic endoscopes may be utilized for stereoscopic viewing of said cavity.

2. A method as set forth in claim 1 involving utilization of a pair of thoracoscopic endoscopes and wherein:

said step of selecting said endoscopes includes selecting thoracoscopic endoscopes;

said step of making said incision includes making said incision in said patient's chest adjacent a lung; and said step of moving said tissue away includes the step of inserting an endotracheal tube and deflating said lung.

\* \* \* \* \*